United States Patent
Schrum et al.

(10) Patent No.: US 8,759,313 B2
(45) Date of Patent: Jun. 24, 2014

(54) TREATMENT OF FIBROSIS USING MICRORNA 19B

(75) Inventors: Laura W. Schrum, Charlotte, NC (US); Ashley M. Lakner, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 13/566,138

(22) Filed: Aug. 3, 2012

(65) Prior Publication Data

US 2013/0053429 A1 Feb. 28, 2013

Related U.S. Application Data

(60) Provisional application No. 61/514,764, filed on Aug. 3, 2011.

(51) Int. Cl.
*C12N 15/113* (2010.01)
*C07H 21/04* (2006.01)

(52) U.S. Cl.
CPC .................................. *C12N 15/113* (2013.01)
USPC ....................................... 514/44 A; 536/24.5

(58) Field of Classification Search
None
See application file for complete search history.

(56) References Cited

U.S. PATENT DOCUMENTS

| | | | |
|---|---|---|---|
| 7,064,127 B2 | 6/2006 | Friedman et al. | |
| 7,888,035 B2 | 2/2011 | Klass et al. | |
| 7,888,498 B2 * | 2/2011 | De Fougerolles et al. | 536/24.5 |
| 7,893,034 B2 | 2/2011 | Slack et al. | |
| 2009/0092974 A1 * | 4/2009 | Davison et al. | 435/6 |
| 2009/0209500 A1 | 8/2009 | Evans et al. | |
| 2011/0053158 A1 | 3/2011 | Mambo et al. | |
| 2011/0190383 A1 * | 8/2011 | Marsh et al. | 514/44 A |

FOREIGN PATENT DOCUMENTS

| | | |
|---|---|---|
| WO | 2009/018493 A1 | 2/2009 |
| WO | 2010/033773 A2 | 3/2010 |

OTHER PUBLICATIONS

Gressner et al. Liver International 2008, vol. 28, pp. 1065-1079.*
De Roos et al. Gene Therapy 1997, vol. 4, pp. 55-62.*
Van Almen et al., "MicroRNA-18 and microRNA-19 regulate CTGF and TSP-1 expression in age-related heart failure", Aging Cell 10:769-79 (2011).
Dews et al., "The Myc-miR-19~92 Axis Blunts TGFbeta Signaling and Production of Multiple TGFbeta-Dependent Antiangiogenic Factors", Cancer Research 70:8233-46 (2010).
Mestdagh et al., "The miR-17-92 MicroRNA Cluster Regulates Multiple Components of the TGF-beta Pathway in Neuroblastoma", Molecular Cell 40:762-73 (2010).
Kodama et al., "Increases in p53 expression induce CTGF synthesis by mouse and human hepatocytes and result in liver fibrosis in mice", The Journal of Clinical Investigation 121(8):3343-56 (2011).
Gui et al., "Serum microRNA characterization identifies miR-885-5p as a potential marker for detecting liver pathologies", Clinical Science 120:183-93 (2011).
Lakner et al., "Inhibitory Effects of MicroRNA 19b in Hepatic Stellate Cell-Mediated Fibrogenesis", Hepatology 56 (1):300-10 (2012).
Pandit et al., "Inhibition and Role of let-7d in Idiopathic Pulmonary Fibrosis", American Journal of Respiratory and Critical Care Medicine 182:220-29 (2010).
Jiang et al., "MicroRNAs and the regulation of fibrosis", FEBS Journal 277:2015-21 (2010).
Sekiya et al., "Suppression of hepatic stellate cell activation by microRNA-29b", Biochemical and Biophysical Research Communications 412:74-79 (2011).
Venugopal et al., "Liver fibrosis causes downregulation of miRNA-150 and miRNA-194 in hepatic stellate cells, and their overexpression causes decreased stellate cell activation", American Journal of Physiology—Gastrointestinal and Liver Physiology 298:G101-G106 (2010).
Lakner et al., "microRNAs: Fad or future of liver disease", World Journal of Gastroenterology 17(20):2536-42 (2011).

* cited by examiner

*Primary Examiner* — Tracy Vivlemore
(74) *Attorney, Agent, or Firm* — Alston & Bird LLP

(57) ABSTRACT

The present invention provides a method for treating or preventing fibrosis comprising administering to a patient in need of such treatment or prevention an amount of microRNA-19b effective to treat or prevent said fibrosis. In some embodiments, the invention relates to inhibiting the activation of collagen-producing cells and thereby treating or preventing fibrosis. The methods of the invention also include detection of biomarkers that can be used to diagnose disease and/or evaluate the prognosis of a patient suffering from fibrosis or at risk of developing fibrosis, such as hepatic fibrosis. Such methods may be used to characterize the progression of diseases associated with fibrosis.

25 Claims, 17 Drawing Sheets

Figures 1A, 1B:
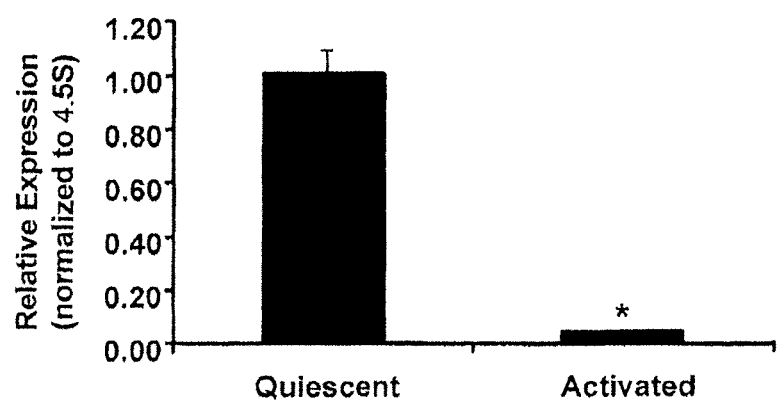

| Probeset ID | p-value (activated vs quiescent) | Fold-Change (activated vs quiescent) |
|---|---|---|
| rno-miR-150_st | 8.2E-09 | -7.5E+01 |
| rno-miR-16_st | 6.3E-06 | -2.2E+00 |
| rno-miR-194_st | 9.0E-05 | -6.7E+01 |
| rno-miR-19a_st | 2.2E-03 | -1.5E+00 |
| rno-miR-19b_st | 2.8E-05 | -6.3E+00 |
| rno-miR-29a_st | 1.9E-04 | -2.5E+00 |
| rno-miR-29b_st | 1.2E-04 | -5.2E+00 |
| rno-miR-29c_st | 5.1E-04 | -3.1E+00 |
| rno-miR-92a_st | 3.1E-05 | -2.0E+00 |

SCR

19b

SEQUENCE LISTING

```
<160> NUMBER OF SEQ ID NOS: 1

<210> SEQ ID NO 1
<211> LENGTH: 23
<212> TYPE: RNA
<213> ORGANISM: Homo sapien
<220> FEATURE:
<223> OTHER INFORMATION: microRNA 19b sequence

<400> SEQUENCE: 1
ugugcaaauc caugcaaaac uga                                              23
```

TREATMENT OF FIBROSIS USING MICRORNA 19B

The present invention claims priority to U.S. Provisional Application No. 61/514,764, filed Aug. 3, 2011, the entire contents of which are incorporated herein by reference.

FIELD OF THE INVENTION

The present invention is directed to compositions and associated methods for the treatment, prevention, and/or amelioration of fibrosis, such as fibrosis of the liver, lung, kidney, pancreas, heart, and/or cardiac fibrosis. In particular, embodiments of the present invention relate to methods of using microRNA-19b (miR-19b) for the treatment of fibrosis.

BACKGROUND OF THE INVENTION

Hepatic fibrosis, the accumulation of abnormal extracellular matrix (ECM) proteins and a resultant loss of liver function, is an accompaniment of an inflammation-driven wound healing process triggered by chronic liver injury. Some of the main causes of liver injury leading to fibrosis include chronic hepatitis C virus (HCV) infection, alcohol abuse, chronic hepatitis B (HBV) infection, iron overload as occurs in hereditary hemochromatosis, and increasingly, non-alcoholic steatohepatitis (NASH).

Fibrosis of the liver is characterized by excessive deposition of ECM components, predominately type I collagen. Cytokine signaling predominates during fibrogenesis serving to initiate activation of resident immune and hepatic stellate cells (HSCs) promoting wound repair. Activated HSCs are the principal cell type promoting synthesis and deposition of ECM proteins in response to increased levels of circulating inflammatory signals derived from damaged parenchymal cells. These resident vitamin A storing cells are found within the perisinusoidal space of Disse in a quiescent state, but upon hepatic injury the HSCs transdifferentiate into myofibroblast-like cells marked by expression of smooth muscle α-actin (αSMA), loss of retinyl ester stores, and increased proliferation and contractility. Myofibroblastic HSCs respond to and secrete a variety of profibrogenic cytokines including connective tissue growth factor, tissue inhibitor of metalloproteinases and transforming growth factor-beta (TGFβ). Of these, TGFβ has been recognized as the most potent fibrogenic cytokine regulating collagen production by the HSC via autocrine and paracrine signaling pathways.

The inflammatory process ensuing from hepatic injury triggers a variety of cellular responses including cell repair, hepatocyte regeneration, increased ECM turnover, and ultimately in some patients significant fibrosis. Disproportionate deposition of fibrillar collagens disrupts normal liver architecture and hepatic function and, if left untreated, may progress to cirrhosis, portal hypertension, and hepatocelluar carcinoma. Cirrhosis is a significant cause of morbidity and mortality worldwide. Accordingly there is an urgent need for antifibrotic therapies designed to impede and/or reverse fibrogenesis.

BRIEF SUMMARY OF THE INVENTION

The invention is based, in part, on the discovery that expression of microRNA-19b (miR-19b) is suppressed in both cells that stimulate fibrosis, particularly activated hepatic stellate cells (HSCs), and fibrotic tissue samples, particularly fibrotic liver samples. The invention is also based, in part, on the discovery that expression of miR-19b suppresses TGFβ signaling and activation of HSCs. Accordingly, in one aspect, the invention provides methods of treating fibrosis in a mammal. The methods comprising administering a therapeutically effective amount of a composition comprising miR-19b, or a precursor or derivative thereof, to the mammal.

In certain embodiments, the miR-19b or precursor thereof comprises the sequence: 5'-UGUGCAAAUCCAUG-CAAAACUGA-3' (SEQ ID NO: 1). In certain embodiments, the composition further comprises at least one microRNA other than miR-19b. In certain embodiments, the other microRNA is selected from the group consisting of let7a, let7d, miR-16, miR-19a, miR-20a, miR-25, miR-26a, miR-29a, miR-29b, miR29c, miR-30a, miR-30a*, miR-30b-5p, miR-30c, miR-30c-2*, miR-30d, miR-30e, miR-34c, miR-92a, miR-99a, miR-101b, miR-106b, miR-122, miR-126, miR-139-3p, miR-139-5p, miR-140*, miR-150, miR-151, miR-184, miR-192, miR-194, miR-195, miR-200b, miR-203, miR-221, miR-322, miR-322*, miR-339-3p, miR-339-5p, miR-361, miR-378, miR-378*, miR-497, miR-500, miR-532-3p, miR-532-5p, miR-872*, and precursors or derivatives thereof. In other embodiments, the other microRNA is selected from the group consisting of miR-16, miR-19a, miR-29a, miR-29b, miR29c, miR-34c, miR-92a, miR-150, miR-184, miR-194, miR-221, and precursors or derivatives thereof. In still other embodiments, the other microRNA is selected from the group consisting of miR-19a, miR-29a, miR-29b, miR29c, miR-92a, and precursors or derivatives thereof. In preferred embodiments, the other microRNA is miR-19a and/or miR-92a, or precursor(s) or derivative(s) thereof. In other preferred embodiments, the other microRNA is miR-29a, miR-29b, and/or miR-29c, or precursor(s) or derivative(s) thereof.

In certain embodiments, the composition comprises a DNA precursor that encodes an RNA comprising miR-19b. In certain embodiments, the DNA is contained in a vector selected from the group consisting of a plasmid, cosmid, phagemid, or virus.

In certain embodiments, the composition comprising miR-19b, or a precursor or derivative thereof, includes a pharmaceutically acceptable carrier. In certain embodiments, the composition comprising miR-19b, or a precursor or derivative thereof, includes a pharmaceutically acceptable carrier comprising a virus, a liposome, or a polymer.

In certain embodiments, the mammal is suffering from liver fibrosis. In certain embodiments, the mammal suffers from at least one of chronic Hepatitis B, Hepatitis C, non-alcoholic steatophepatitis (NASH), alcoholic liver disease, a metabolic liver disease, Wilson's disease, hemochromatosis, or biliary obstruction. In certain embodiments, the mammal is suffering from cardiac fibrosis or lung, pancreas, kidney, or heart fibrosis. In certain embodiments, the methods comprise the step of perfusing the composition comprising the miR-19b through a targeted tissue of the mammal. In certain embodiments, the mammal is a human.

In certain embodiments, the composition inhibits expression of a gene in a cell type that promotes said fibrosis, wherein the gene is selected from the group consisting of transforming growth factor beta (TGFβ) receptor II (TGF-βRII), RSMAD3, Collagen 1α1 (Col1α1), Collagen 1α2 (Col1α2), smooth muscle α-actin (αSMA), MeCP2, Furin, CTGF, THBS1 and KLF10. In certain embodiments, the gene expression is inhibited by at least 10%, 15%, 20%, 25%, 30%, 35%, 40%, 45%, 50%, 55%, 60%, 65%, 70%, 75%, 80%, 85%, 90%, 95%, or more. In certain embodiments, the composition inhibits expression of a protein in a cell type that promotes said fibrosis, wherein the protein is selected from the group consisting of TGFβRII, Type I Collagen, αSMA, MeCP2, Furin, CTGF, THBS1 and KLF10. In certain embodiments, the protein expression is inhibited by at least 10%, 20%, 30%, 40%, 50%, 60%, 70%, or more. In certain embodiments, the cell type is a collagen-producing cell (e.g., a collagen-producing fibroblast). In certain related embodiments, the cell type is a HSC. In other related embodiments, the cell type is a collagen-producing cell found in the lung, pancreas, kidney, heart, or cardiac tissues.

In another aspect, the invention provides methods for inhibiting activation of a HSC. In certain embodiments, the methods comprise contacting an HSC with a composition comprising miR-19b or a precursor or derivative thereof. In certain embodiments, the miR-19b or precursor thereof comprises the sequence: 5' UGUGCAAAUCCAUG-CAAAACUGA-3'(SEQ ID NO: 1). In certain embodiments, the composition comprises a DNA precursor that encodes miR-19b. In certain embodiments, the amount of miR-19b, or precursor or derivative thereof, in the composition is at least 25 nM, at least 50 nM, or preferably at least 75 nM. In certain embodiments, the composition comprises a carrier selected from the group consisting of a virus, a liposome, and a polymer.

In certain embodiments, the composition comprises at least one microRNA other than miR-19b. In certain embodiments, the other microRNA is selected from the group consisting of let7a, let7d, miR-16, miR-19a, miR-20a, miR-25, miR-26a, miR-29a, miR-29b, miR29c, miR-30a, miR-30a*, miR-30b-5p, miR-30c, miR-30c-2*, miR-30d, miR-30e, miR-34c, miR-92a, miR-99a, miR-101b, miR-106b, miR-122, miR-126, miR-139-3p, miR-139-5p, miR-140*, miR-150, miR-151, miR-184, miR-192, miR-194, miR-195, miR-200b, miR-203, miR-221, miR-322, miR-322*, miR-339-3p, miR-339-5p, miR-361, miR-378, miR-378*, miR-497, miR-500, miR-532-3p, miR-532-5p, miR-872*, and precursors and derivatives thereof In other embodiments, the other microRNA is selected from the group consisting of miR-16, miR-19a, miR-29a, miR-29b, miR29c, miR-34c, miR-92a, miR-150, miR-184, miR-194, miR-221, and precursors and derivatives thereof. In still other embodiments, the other microRNA is selected from the group consisting of miR-19a, miR-29a, miR-29b, miR29c, miR-92a, and precursors or derivatives thereof. In preferred embodiments, the other microRNA is miR-19a and/or miR-92a, or precursor(s) or derivative(s) thereof. In other preferred embodiments, the other microRNA is miR-29a, miR-29b, and/or miR-29c, or precursor(s) or derivative(s) thereof.

In certain embodiments, the composition inhibits expression of at least one gene in the HSC, wherein the gene is selected from the group consisting of TGFβRII, RSMAD3, Collagen 1α1 (Col1=1), Collagen 1α2 (Col1α2), smooth muscle α-actin (αSMA), MeCP2, Furin, CTGF, THBS1 and KLF10. In certain embodiments, the expression of the gene is inhibited by at least 10%, 15%, 20%, 25%, 30%, 35%, 40%, 45%, 50%, 55%, 60%, 65%, 70%, 75%, 80%, 85%, 90%, 95%, or more. In certain embodiments, the composition inhibits expression of at least one protein in the HSC, wherein the protein is selected from the group consisting of TGFβRII, Type I Collagen, αSMA, MeCP2, Furin, CTGF, THBS1 and KLF10. In certain embodiments, the expression of the protein is inhibited by at least 10%, 20%, 30%, 40%, 50%, 60%, 70%, or more.

In another aspect, the invention provides methods for inhibiting expression of TGFβRII or inhibiting TGFβ signaling in a cell. In certain embodiments, the methods comprise contacting the cell with a composition comprising miR-19b or a precursor or derivative thereof. In certain embodiments, the miR-19b or precursor thereof comprises the sequence: 5' UGUGCAAAUCCAUGCAAAACUGA-3'(SEQ ID NO: 1). In certain embodiments, the composition comprises a DNA precursor that encodes the miR-19b. In certain embodiments, the amount of miR-19b, or precursor or derivative thereof, in the composition is at least 25 nM, at least 50 nM, or preferably at least 75 nM. In certain embodiments, the composition comprises a carrier selected from the group consisting of a virus, a liposome, and/or a polymer.

In certain embodiments, the composition further comprises at least one microRNA or derivative thereof other than miR-19b. In certain embodiments, the other microRNA is selected from the group consisting of miR-16, miR-19a, miR-29a, miR-29b, miR29c, miR-92a, miR-150, miR-194, and precursors or derivatives thereof. In certain embodiments, the other microRNA is selected from the group consisting of miR-19a, miR-29a, miR-29b, miR29c, miR-92a, and precursors or derivatives thereof. In certain embodiments, the other microRNA is miR-29a, miR-29b, and/or miR-29c, or precursor(s) or derivative(s) thereof. In certain embodiments, the composition does not comprise any microRNAs of the miR-17-92 cluster other than miR-19b.

In certain embodiments, the cell is a collagen-producing cell. In certain embodiments, the cell is a fibroblast (e.g., a collagen-producing fibroblast). In certain embodiments, the cell is a liver cell, preferably a HSC. In certain embodiments, the cell is a lung, pancreas, kidney, heart, or cardiac cell (e.g., a fibroblast or collagen-producing cell found in the lung, pancreas, kidney, heart, or cardiac tissues). In certain embodiments, the cell is not a neuroblastoma cell.

In another aspect, the invention provides methods for characterizing fibrosis in a patient. In certain embodiments, the methods comprise measuring a level of miR-19b in a blood or tissue sample from the patient and determining whether the level of miR-19b in the sample is decreased or elevated as compared to a control sample. In certain embodiments, the blood sample is serum or plasma sample. In certain embodiments, the tissue sample is a liver biopsy. In other embodiments, the tissue sample is a lung, pancreas, kidney, heart, or cardiac biopsy. In certain embodiments, the control sample is a corresponding blood or tissue sample from a patient that does not have fibrosis.

In certain embodiments, an increased level of miR-19b in a blood sample (e.g., serum or plasma sample) and/or a decreased level of miR-19b in a tissue sample (e.g., liver, lung, pancreas, kidney, heart, or cardiac biopsy) indicates that the patient is suffering from fibrosis. In certain embodiments, the fibrosis is hepatic fibrosis. In certain embodiments, the patient suffers from at least one of chronic Hepatitis B, Hepatitis C, non-alcoholic steatophepatitis (NASH), alcoholic liver disease, a metabolic liver diseases, Wilson's disease, hemochromatosis, or biliary obstruction. In other embodiments, the methods are used to characterize the progression of diseases associated with lung, pancreas, kidney, heart, or cardiac fibrosis.

Additional aspects and details of the invention will be made evident from the detailed description that follows.

BRIEF DESCRIPTION OF THE SEVERAL VIEWS OF THE DRAWING(S)

Figure 1C:
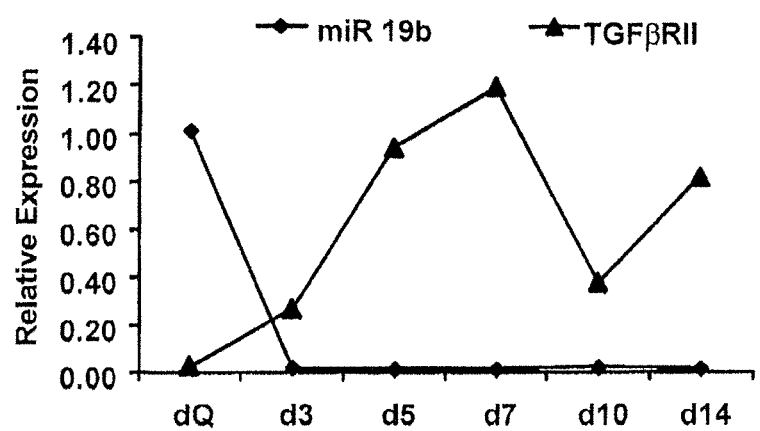

Having described the invention in general terms, reference will now be made to the accompanying drawings, which are not necessarily drawn to scale, and wherein:

FIGS. 1A-1C: Differential miRNA Expression in Quiescent and Activated HSCs. FIG. 1A is a table showing differentially expressed miRNAs as analyzed in freshly isolated and day 14 culture-activated HSCs. FIG. 1B is a bar graph showing qRT-PCR analysis of miR-19b expression in quiescent (n=7) compared to activated (n=6) HSCs. FIG. 1C is a graph illustrating qRT-PCR analysis of miR-19b and TGF-βRII expression levels over days in culture (n=3) as normalized to 4.5S rRNA and β-actin, respectively.

Figure 2A:
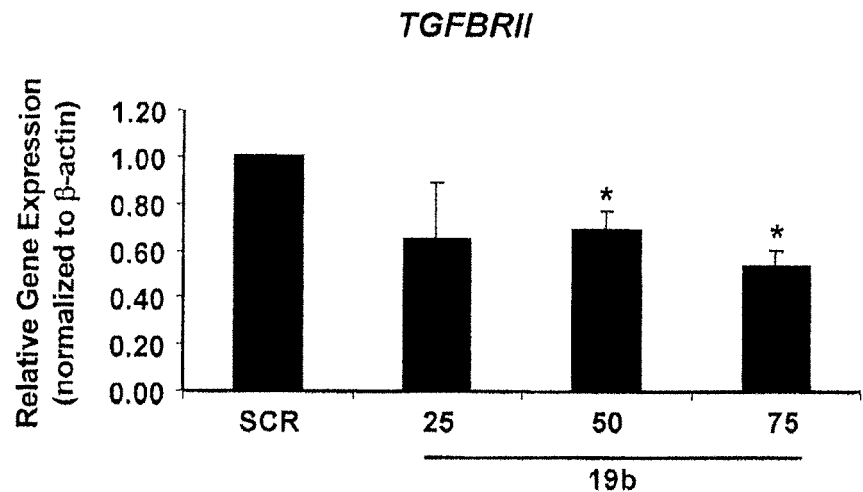
Figure 2B:
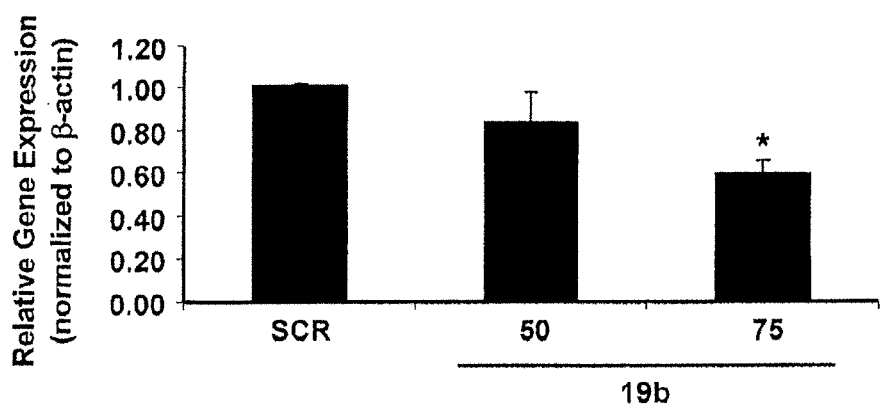
Figure 2C:
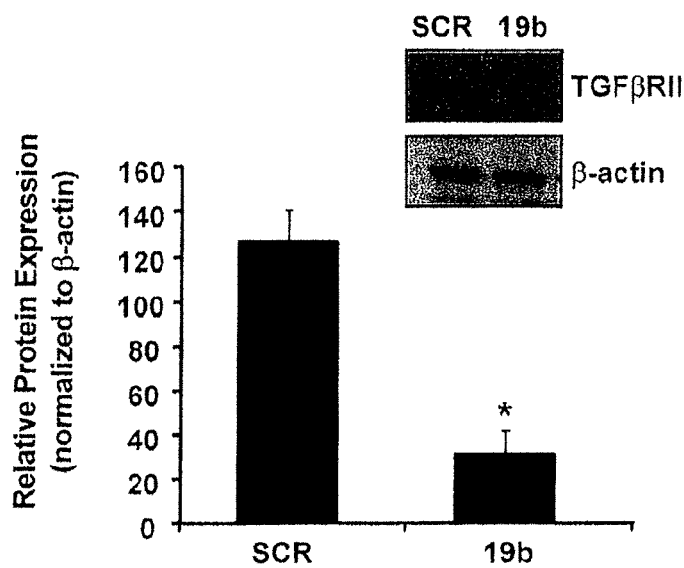
Figure 2D:
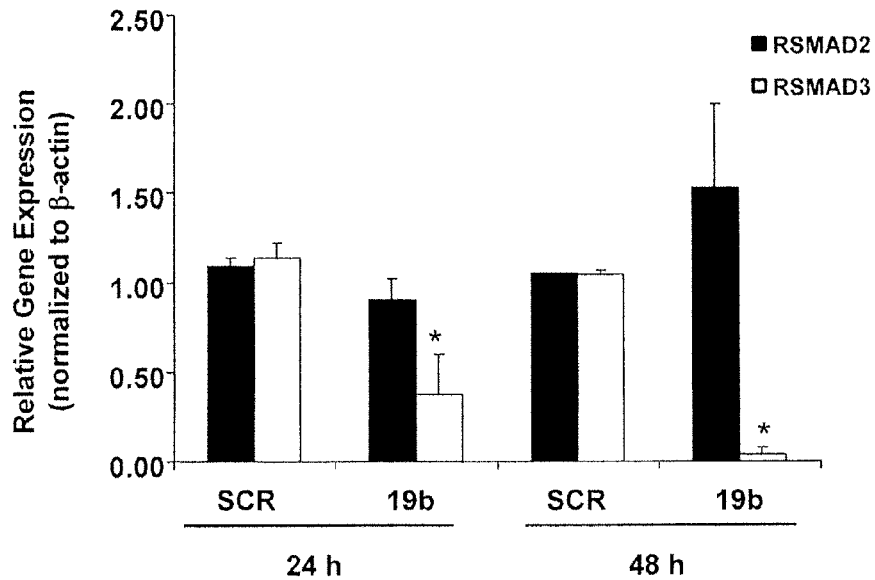
Figure 2E:
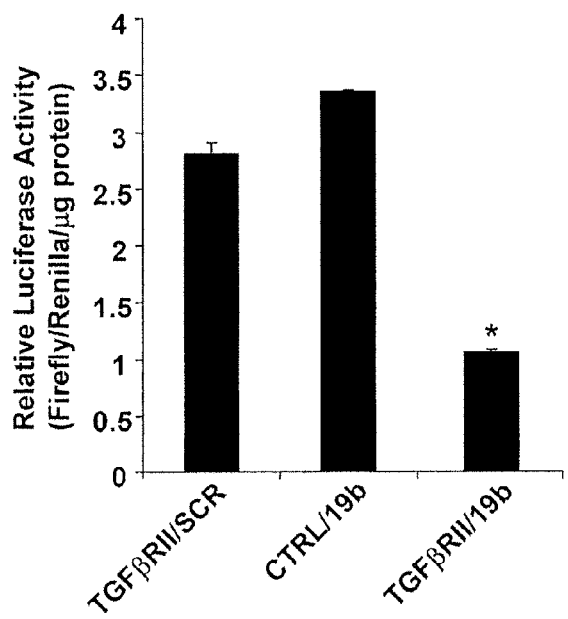

FIGS. 2A-D: miR-19b Negatively Regulates TGFβRII Expression. FIGS. 2A and 2B shows qRT-PCR analysis of TGFβRII gene expression as normalized to β-actin following 24 and 48 hrs, respectively, of transient transfection with miR-19b mimic (25-75 nM) (n=4). FIG. 2C is a representative immunoblot and quantitative densitometry of TGFβRII protein expression 48 hrs post-transfection (miR 19b, 75 nM) (n=3). FIG. 2D shows qRT-PCR analysis of RSMAD gene expression in activated HSCs transfected with mature miR-19b for 24 and 48 hrs. FIG. 2E shows inhibition of firefly luciferase activities of pEZX-TGFβRII reporter by miR-19b mimic. LX-2 cells were co-transfected with 4.8 μg of pEZX-TGFβRII reporter plasmid or empty vector and 75 nM miR-19b or SCR using Lipofectamine 2000.

Figure 3A:
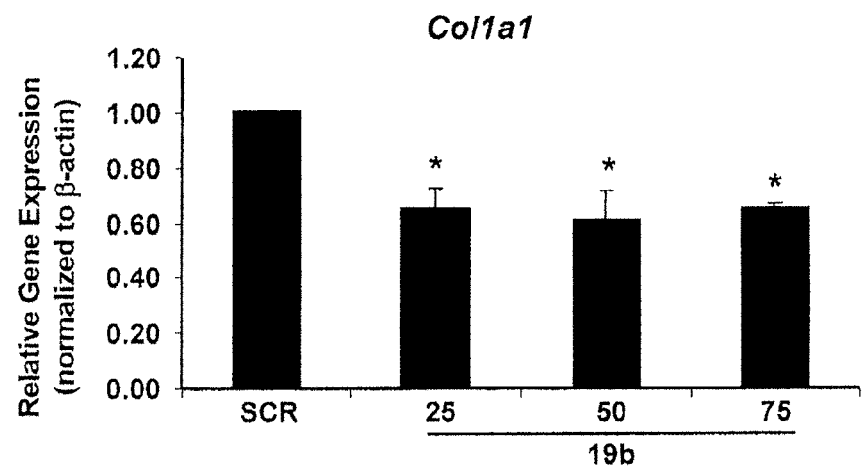
Figure 3B:
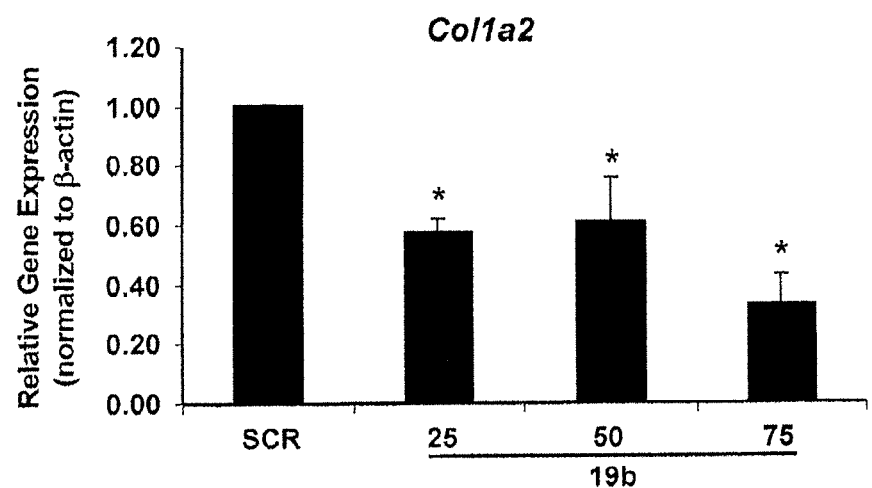
Figure 3C:
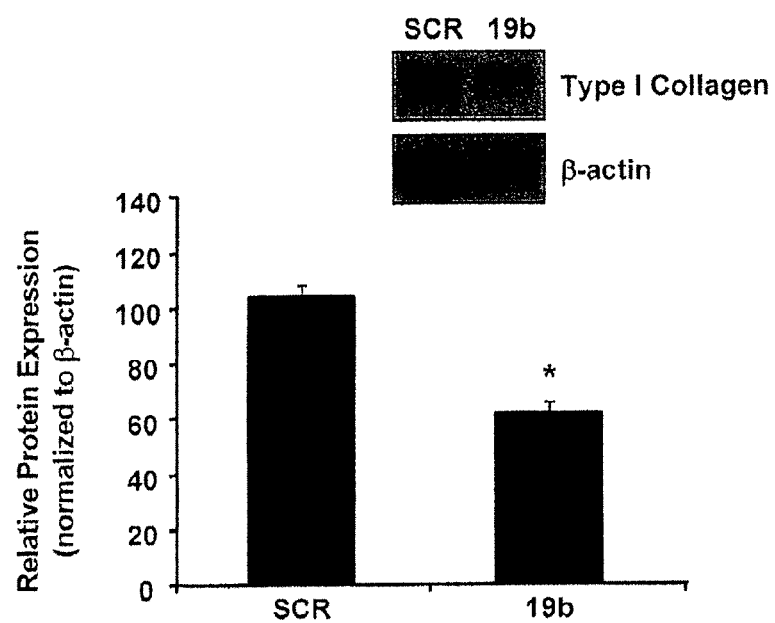

FIGS. 3A-C: miR-19b Exerts Inhibitory Effects on TGFβ Target Gene Collagen. FIGS. 3A and B show qRT-PCR of procollagen mRNA levels in activated HSCs transfected with miR-19b (24 hrs, n=4). FIG. 3C shows a representative immunoblot and quantitative densitometry of type I collagen protein expression 48 hrs post-transfection (n=3).

Figure 4:
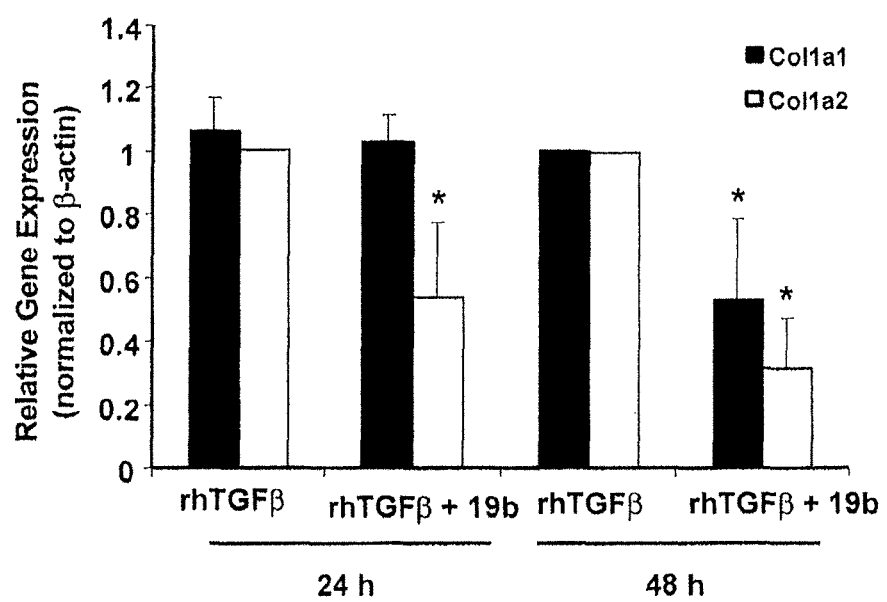

FIG. 4: miR-19b Inhibits Paracrine TGFβ Signals. qRT-PCR analysis of procollagen mRNA levels (n=3). Activated HSCs were transfected with or without miR-19b mimic (75 nM). Following standard 6 hr incubation, transfection medium was removed and fresh culture medium devoid of antibiotic was added that contained 5 ng/ml of recombinant TGFβ (rhTGFβ) for a period of 48 hrs.

Figure 5A:
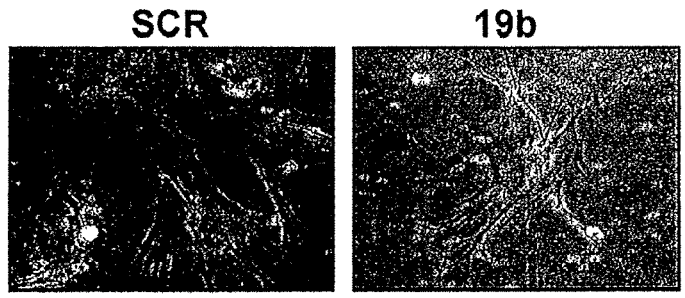
Figure 5B:
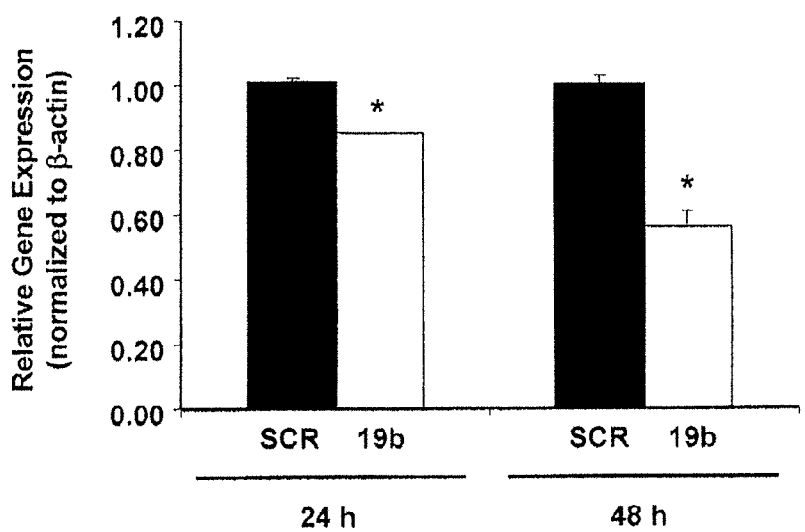
Figure 5C:
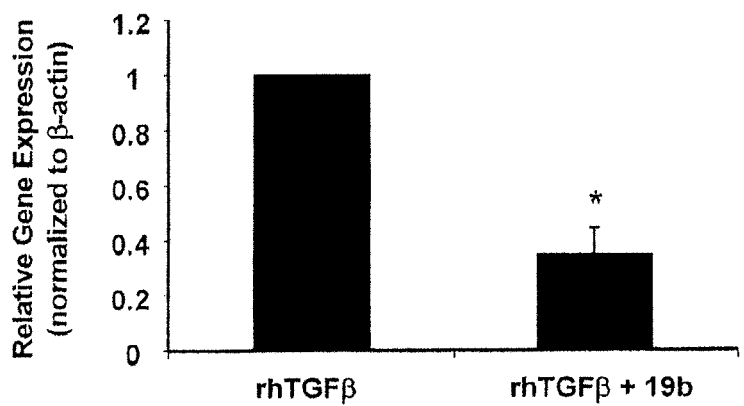
Figure 5D:
Figure 5D:
Figure 5E:
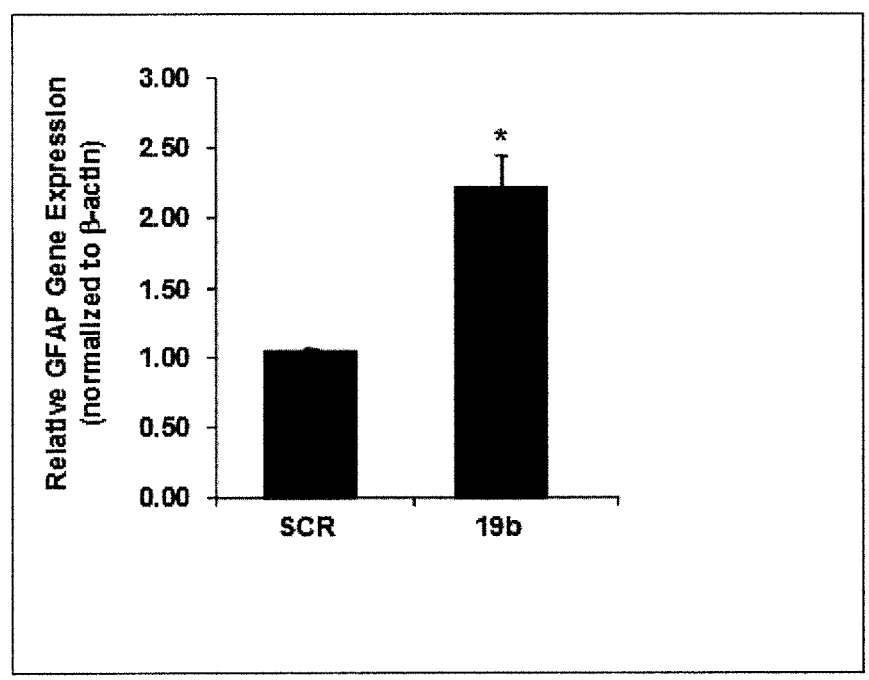
Figure 5F:
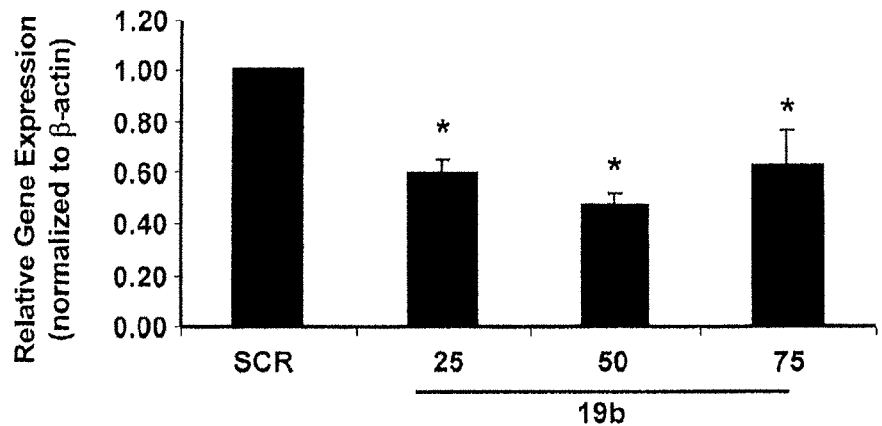
Figure 5G:
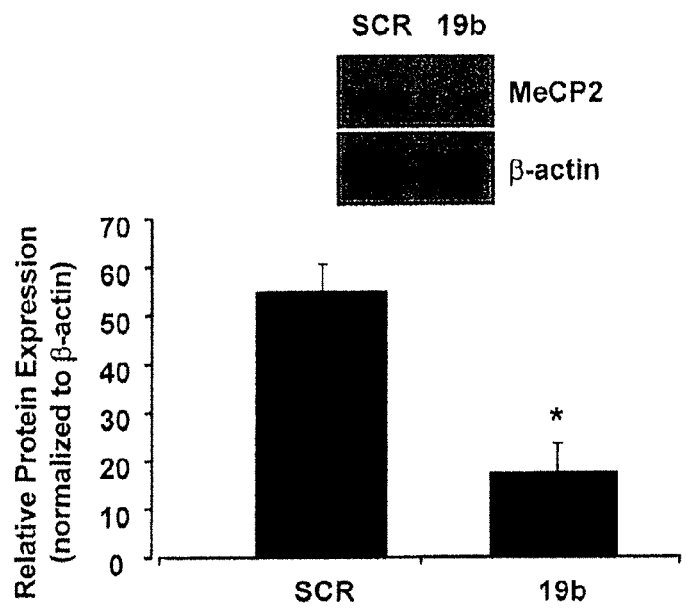

FIGS. 5A-G: HSC Activation is Inhibited by miR-19b. FIG. 5A shows representative light micrographs of activated HSCs transfected with negative control (SCR) or miR-19b (75 nM) after 48 hrs. FIG. 5B shows qRT-PCR analysis of αSMA expression in miR-19b transfected cells at 24 and 48 hrs (n=3). FIG. 5C shows αSMA gene expression in HSCs transfected with miR-19b and subsequently treated with rhTGFβ for 48 hrs. FIG. 5D shows representative images (40×) of fluorescent immunocytochemical analysis of αSMA expression in activated HSCs following 48 hrs of transfection with SCR or miR-19b mimic (75 nM); dapi staining was used to indicate cell nuclei (n=3). FIG. 5E shows GFAP expression in HSCs 48 hrs after transfection with SCR or miR-19b mimic (75 nM). FIG. 5F shows MeCP2 gene expression as measured by qRT-PCR following 24 hrs of miR-19b transfection in activated HSCs (n=4). FIG. 5G shows representative immunoblot and quantitative densitometry of MeCP2 protein expression in HSCs following 48 hrs of miR-19b (75 nM, n=3).

Figure 6A:
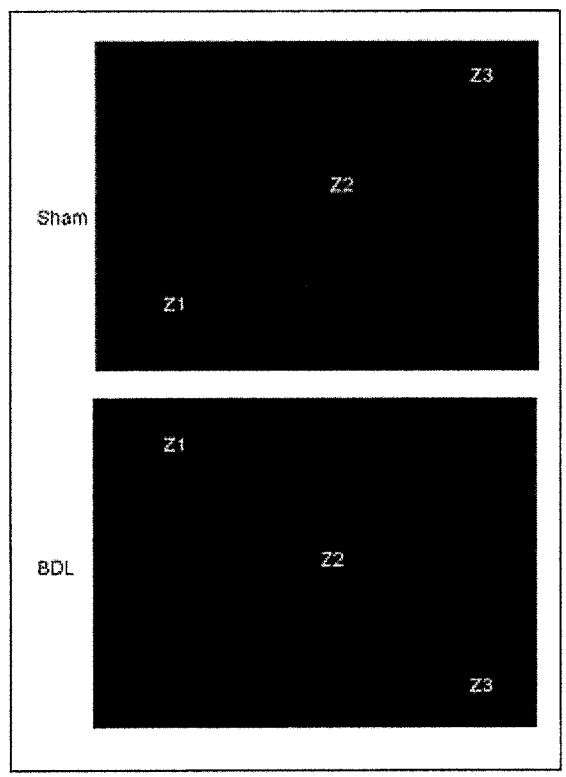
Figure 6B:
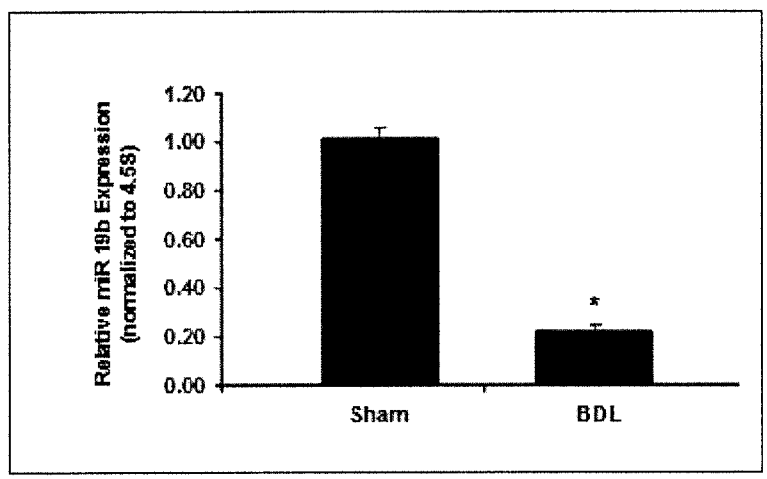
Figures 6C, 6D:
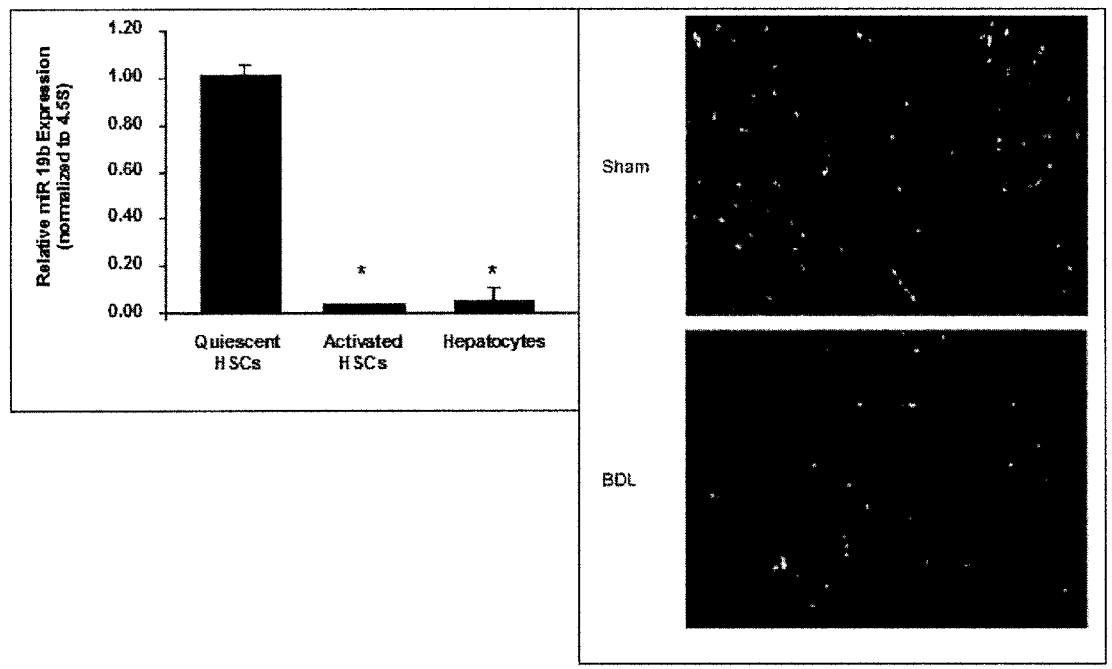

FIGS. 6A-F: Downregulation of miR-19b in Rodent Models of Hepatic Fibrosis. FIG. 6A shows representative immunofluorescent images of sham (normal) and BDL (fibrotic) tissue sections following in situ hybridization with double DIG labeled LNA miR-19b probes. miR-19b expression levels are marked by fluorescence. Zonal damage (Z1, Z2, Z3) is indicated. FIG. 6B shows qRT-PCR results for miR-19b in liver samples harvested from rats which underwent BDL or Sham surgeries. FIG. 6C shows qRT-PCR results for miR-19b in quiescent HSCs, activated HSCs, and primary rat hepatocytes. FIG. 6D shows co-localization of miR-19b and a quiescent HSC specific marker (GFAP). Upon merging the immunofluorescent images, overlapping fluorescence identifies quiescent HSCs expressing miR-19b in sham and BDL tissue sections. Data are presented as mean±SE. *Differs from sham, p<0.05.

Figure 7A:
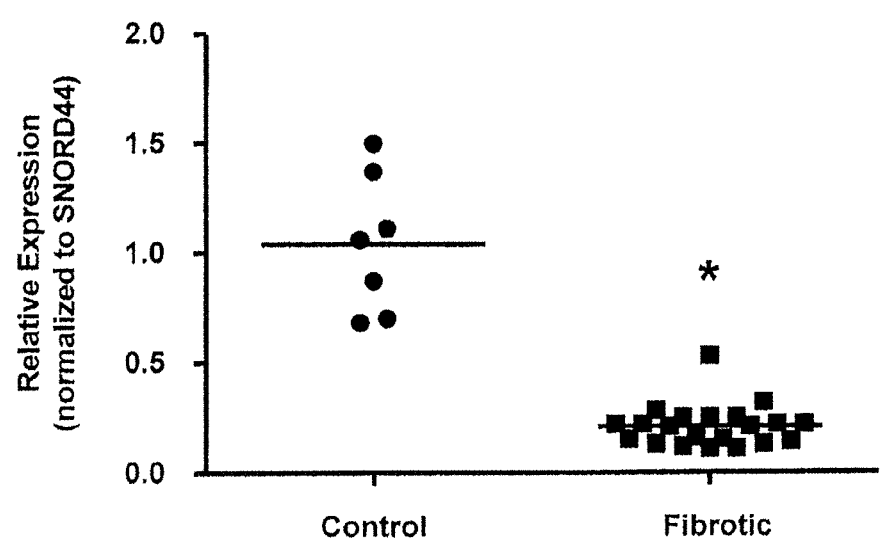
Figure 7B:
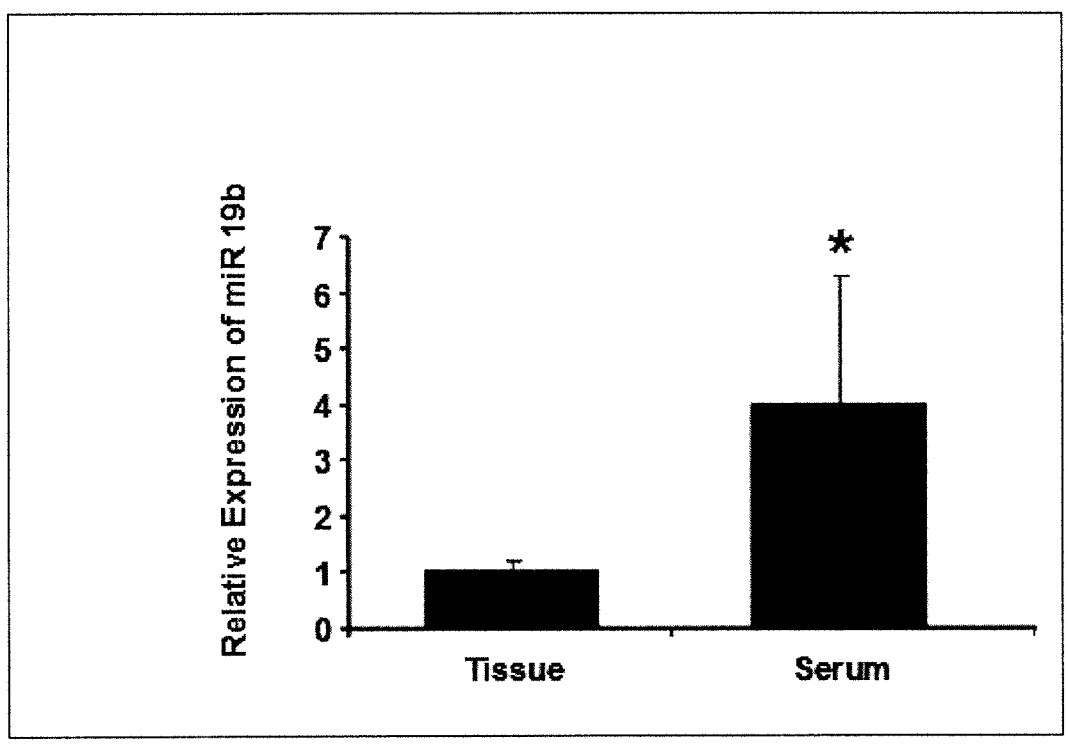

FIGS. 7A-B: miR-19b Expression is Decreased in Human Fibrotic Livers. FIG. 7A shows qRT-PCR analysis of miR-19b expression levels in fibrotic liver tissue (n=21) as compared to normal controls (n=7). FIG. 7B shows qRT-PCR analysis of miR-19b levels in sera of fibrotic patients.

Figure 8:
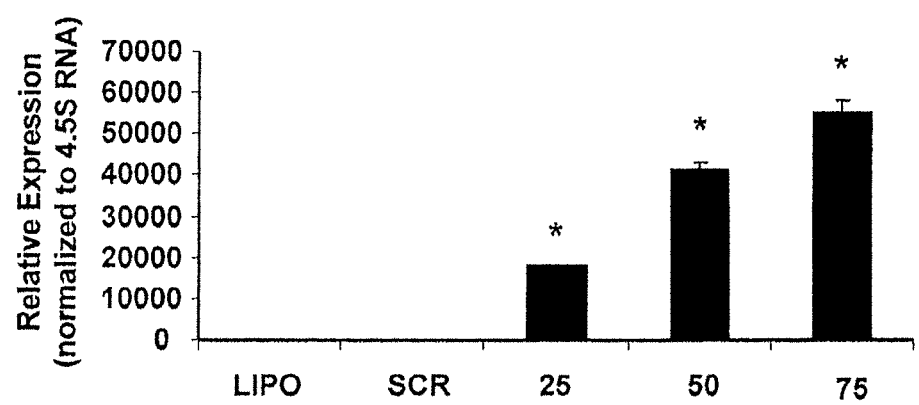

FIG. 8: Efficient Transfection of miR-19b in Activated HSCs. Representative qRT-PCR analysis of miR-19b expression in HSCs transfected with Lipofectamine 2000 alone (LIPO), negative control (SCR), or mature miR-19b (25-75 nM) for 24 hrs. Expression was normalized to 4.5S rRNA.

Figure 9:
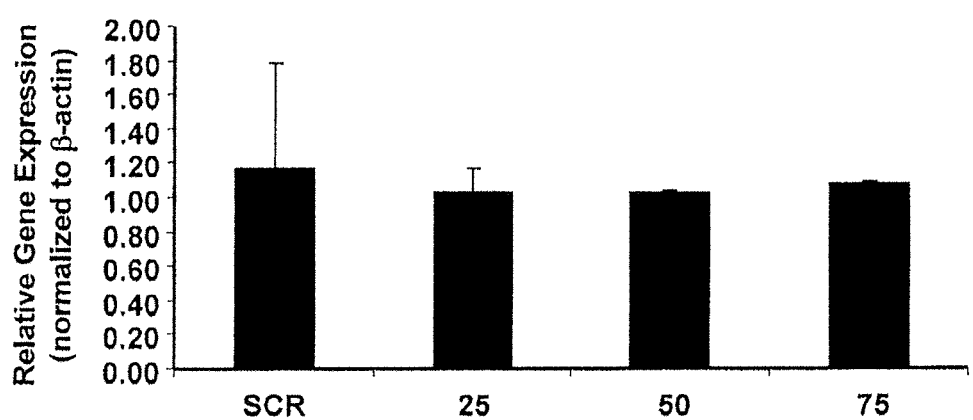

FIG. 9: miR-19b Does Not Regulate SMAD4 Expression in Activated HSCs. qRT-PCR analysis of SMAD4 gene expression following 24 hrs of miR-19b transfection studies as normalized to levels of β-actin (n=3).

Figure 10:
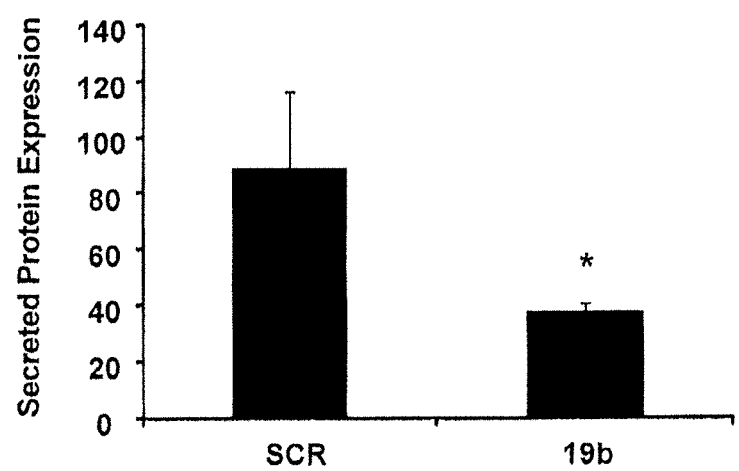

FIG. 10: Collagen Secretion is Inhibited by miR-19b in Activated HSCs. Quantitative densitometry of immunoblot analyses of secreted type I collagen protein expression following 48 hrs of miR-19b transfection. Culture medium was harvested following 48 hrs and proteins concentrated using Nanosep tubes (Pall Corporation; Ann Arbor, Mich.) (n=3).

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention are directed to the treatment and/or prevention of fibrosis, in particular hepatic fibrosis, by downregulating the expression of various fibrogenic mediators. In the liver, such fibrogenic mediators stimulate the activation and proliferation of collagen-producing cells, including hepatic stellate cells (HSCs). In particular, embodiments of the present invention are directed to methods for the treatment of cells (e.g., collagen-producing cells) or a mammal suffering from fibrosis by administering a therapeutically effective amount of microRNA-19b (miR-19b). Other embodiments of the invention include inhibiting TGFβRII expression and/or TGFβ signaling in a cell by contacting the cell with an effective amount of miR-19b.

MicroRNAs (referred to as "miRNAs") are small non-coding RNAs, belonging to a class of regulatory molecules found in plants and animals that control gene expression by binding to complementary sites on target messenger RNA (mRNA) transcripts. miRNAs are generated from larger RNA precursors (termed pri-miRNAs) that are processed in the nucleus into approximately 70 nucleotide pre-miRNAs, which fold into imperfect stem-loop structures. The pre-miRNAs undergo an additional processing step within the cytoplasm where mature miRNAs of 18-25 nucleotides in length are excised from one side of the pre-miRNA hairpin by an RNase III enzyme.

miRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the RISC complex. In the second mechanism, miRNAs that bind to imperfect complementary sites on messenger RNA transcripts direct gene regulation at the posttranscriptional level but do not cleave their mRNA targets. miRNAs identified in both plants and animals use this mechanism to exert translational control over their gene targets.

As used herein, the term "microRNA" (miRNA or miR) includes mature single stranded miRNAs, precursor miRNAs (pre-miR), and variants thereof, which may be naturally occurring. In some instances, the term "miRNA" also includes primary miRNA transcripts and duplex miRNAs. Unless otherwise noted, when used herein, the name of a specific miRNA refers to the mature miRNA of a precursor miRNA. For example, miR-19b refers to a mature miRNA sequence derived from pre-miR-19b.

Compositions useful in the methods of the invention include compositions comprising miR-19b or a precursor thereof comprising the following sequence: 5'-UGUGCAAAUCCAUGCAAAACUGA-3'(SEQ ID NO: 1). The precursor can be, for example, pre-miR-19b, pri-miR-17-92, pri-miR-106a-363, or any other RNA that can be processed by a cell to produce miR-19b. In other embodiments, the compositions comprise a DNA precursor that encodes miR-19b, pre-miR-19b, pri-miR-17-92, pri-miR-106a-363, or any other RNA that can be processed by a cell to produce mature miR-19b. In still other embodiments, the compositions comprise a miR-19b analog. As used herein, the terms "analog" and "derivative" are used interchangeably to refer to a microRNA, or DNA or RNA precursor thereof, that comprises one or more differences relative to naturally-occurring miR-19b. In certain embodiments, the analog comprises one or more nucleobase alterations. Preferably, the nucleobase alteration does not change the seed sequence of miR-19b (i.e., the eight 5'-most nucleobases of SEQ ID NO: 1) or functionally alter the secondary structure and/or processing of a precursor RNA. In other embodiments, the analog comprises one or more backbone alterations, such as a pyrimidine comprising a 2'-fluoro ribose structure, a C5-halogenated pyrimidine, a phosphorothioate group, or a 2'-O-methyl ribose structure (e.g., at position 2 from the 5' end of miR-19b). In still other embodiments, the analog is covalently linked to a carrier, such as cholesterol, that improves cellular delivery and/or uptake of the microRNA. The structural requirements of microRNA function have been extensively studied in the art, providing guidance on how to design suitable miR-19b analogs and precursors thereof that can be used in the methods of the invention. See, e.g., T. Rana (2007), Nature Reviews, Molecular Cell Biology, Vol. 8:23-36; Krol et al. (2004), JBC, Vol. 279(40):42230-39.

Following exposure to a fibrogenic stimulus, numerous changes in cellular organization, gene expression and overall organ function can be observed within the affected tissue. For example, in the liver, damage to liver parenchyma results in both necrosis and apoptosis of hepatocytes, with subsequent release of inflammatory mediators. Cytokine signaling predominates post-insult and evokes the activation of HSCs. While a wide range of soluble factors are implicated as fibrotic mediators, transforming growth factor beta (TGFβ) is considered the most potent stimulus for HSC-mediated fibrogenesis and collagen deposition. Upon activation TGFβ binds to the heteromeric receptor complex containing TGFβ type I (TGFβRI) and II (TGFβRII) receptors, and both autocrine and paracrine signaling propagate through the SMAD family of transcriptional activators. Following liver injury, both blood and tissue TGFβ levels are elevated, stimulating the fibrotic response and establishment of the activated phenotype of the HSC.

Increased synthesis and deposition of type I collagen by activated HSCs is ultimately a major cause of organ dysfunction in hepatic fibrosis. In the normal liver, HSCs reside in a quiescent state, functioning to store vitamin A, modulating microcirculation, and regulating ECM production. Following injury, HSCs transdifferentiate into an activated myofibroblast-like cell characterized by loss of vitamin A droplets, changes in cytoskeletal protein expression, including smooth muscle α-actin (αSMA), and hypercontractility leading to decreased sinusoidal blood flow. Initiation of HSC activation is concomitant with the presence of several inflammatory and immunomodulatory molecules. TGFβ is the most potent profibrotic cytokine among those inflammatory molecules known to regulate activated HSCs. Increased TGFβ stimulates procollagen gene expression and other downstream profibrotic targets including matrix degrading proteins. TGFβ signal transduction plays a critical role in both establishment of the myofibroblast phenotype in HSCs, as it directly upregulates profibrotic hallmarks αSMA and collagen, and progression to the disease state. In addition to paracrine stimulation, endogenous TGFβ synthesis is markedly increased as a result of HSC activation, underscoring the importance of this signaling cascade in the progression of hepatic fibrosis.

The present inventors have discovered that miR-19b acts as an inhibitor of TGFβ signaling in HSCs and, in particular, can reduce the expression of transforming growth factor beta receptor II (TGFβRII) as well as other pro-fibrotic targets that are associated with collagen expression. Significant downregulation of miR-19b was observed in culture-activated HSCs, as well as in rodent models of fibrosis and human fibrotic tissue. Conversely, forced expression of the mature miR-19b in activated HSCs significantly reduced the expression of TGFβRII at both the transcriptional and translational levels. Canonical signaling propagated by the SMAD pathway was also subject to regulation by miR-19b, with decreases in SMAD3 mRNA observed. Consistent with TGFβRII's important role in activation of downstream profibrotic gene expression, levels of procollagen mRNA and fully formed type I collagen were also markedly reduced by increased levels of miR-19b. In addition to regulating profibrotic gene expression, changes in hallmarks of HSC activation were also observed, with significant reductions seen in αSMA expression and reversion to a more quiescent phenotype. Accordingly, treatment with miR-19b holds clinical promise as a therapeutic molecule in the treatment and prevention of fibrosis. Up-regulating miR-19b directly or providing analogous pharmaceutical compounds exogenously that increase miR-19b levels should provide an effective therapy for fibrosis resulting from HSC activation or over-expression of TGFβRII and other pro-fibrotic targets associated with collagen expression.

In addition to miR-19b having a direct effect on key transcripts regulating HSC activation, it has also been shown that miR-19b can exert indirect inhibitory actions on transdifferentiation. For instance, increased miR-19b expression was observed to significantly decrease MeCP2 mRNA and protein levels which are necessary to suppress the quiescent phenotype of the cell. miR-19b is thus a critical regulator of HSC-mediated fibrogenesis, by impeding classical TGFβ signaling and through additional effects on epigenetic HSC transdifferentiation factors.

miR-19b or an analog thereof can be chemically synthesized, transcribed in vitro from a DNA template, or transcribed in vivo from an engineered miRNA precursor. Additionally, miR-19b can be expressed in vivo through the use of a DNA precursor, such as a viral vector. Adeno-associated viruses (AAV) are currently in use for several clinical trials, including Duchenne's muscular dystrophy (NCT00428935), Pompe Disease (NCT00976352) and Parkinson's Disease (NCT00643890), and can be adapted for use in the present invention. Knowledge of miRNA genes allows for modification of cells to permit or increase expression of an endogenous miR-19b. Cells can be modified (e.g., by homologous recombination) to provide increased miRNA expression by replacing, in whole or in part, the naturally occurring promoter with all or part of a heterologous promoter so that the cells express the miRNA at higher levels. The heterologous promoter may be inserted in such a manner that it is operatively linked to the desired miRNA encoding sequences. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also may be engineered to express an endogenous gene comprising the miRNA under the control of inducible regulatory elements, in which case the regulatory sequences of the endogenous gene may be replaced by homologous recombination. Gene activation techniques are described, e.g., in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al.

In some embodiments, the miR-19b may be prepared by culturing transformed host cells under culture conditions suitable to express the miR-19b. The resulting expressed miR-19b may then be purified from such culture (i.e., from culture medium or cell extracts) using known purification processes, such as gel filtration and ion exchange chromatography. Purification of the miR-19b may also include an affinity column containing agents which will bind to the nucleic acid; one or more column steps over such affinity resins as concanavalin A-agarose, Heparin-Toyopearl™ or Cibacrom blue 3GA SEPHAROSE™; and/or one or more steps involving hydrophobic interaction chromatography using such resins as phenyl ether, butyl ether, or propyl ether; immunoaffinity chromatography, or complementary cDNA affinity chromatography.

In other embodiments, the miR-19b can be expressed as a product of transgenic animals, which are characterized by somatic or germ cells containing a nucleotide sequence encoding the miRNA. A vector containing DNA encoding a corresponding miRNA and appropriate regulatory elements can be inserted in the germ line of animals using homologous recombination (Capecchi, Science 244:1288-1292 (1989)), such that they express the miRNA. Transgenic animals, preferably non-human mammals, can be produced using methods as described in U.S. Pat. No 5,489,743 to Robinson, et al., and PCT Publication No. WO 94/28122 by Ontario Cancer Institute. miR-19b can be isolated from cells or tissue isolated from transgenic animals as discussed above.

In a preferred embodiment, the miR-19b can be obtained synthetically, for example, by chemically synthesizing a nucleic acid by any method of synthesis known to the skilled artisan. The synthesized miRNA can then be purified by any method known in the art. Methods for chemical synthesis of nucleic acids include, but are not limited to, in vitro chemical synthesis using phosphotriester, phosphate or phosphoramidite chemistry and solid phase techniques, or via deosynucleoside H-phosphonate intermediates (see U.S. Pat. No. 5,705,629 to Bhongle).

For diagnostic or therapeutic applications, the miRNA molecules are preferably provided in the form of a pharmaceutical composition. This pharmaceutical composition typically comprises as an active agent at least one nucleic acid molecule (e.g., miR-19b) as described above and optionally a pharmaceutically acceptable carrier.

Methods for treatment or prevention of at least one symptom or manifestation of fibrosis are also described comprising the administration of an effective amount of a composition containing miR-19b or a precursor or analog thereof to alleviate at least one symptom or decrease at least one manifestation associated with fibrosis. In a preferred embodiment, the fibrosis is hepatic fibrosis. The compositions described herein can be administered in effective dosages alone or in combination with other therapies, such as, immunotherapy, hormone therapy and the like to provide a beneficial effect, e.g., reduce collagen matrix, reduce collagen, or otherwise improve at least one symptom or manifestation of the disease. Alternatively, or in addition, the compositions described herein can be administered in effective dosages in combination with at least one other miRNA or precursor or derivative thereof. Examples of other miRNAs include let7a, let7d, miR-16, miR-19a, miR-20a, miR-25, miR-26a, miR-29a, miR-29b, miR29c, miR-30a, miR-30a*, miR-30b-5p, miR-30c, miR-30c-2*, miR-30d, miR-30e, miR-34c, miR-92a, miR-99a, miR-101b, miR-106b, miR-122, miR-126, miR-139-3p, miR-139-5p, miR-140*, miR-150, miR-151, miR-184, miR-192, miR-194, miR-195, miR-200b, miR-203, miR-221, miR-322, miR-322*, miR-339-3p, miR-339-5p, miR-361, miR-378, miR-378*, miR-497, miR-500, miR-532-3p, miR-532-5p, and miR-872*. In certain embodiments, the other microRNA is selected from the group consisting of miR-16, miR-19a, miR-29a, miR-29b, miR29c, miR-92a, miR-150, miR-194, and precursors or derivatives thereof. In certain embodiments, the other microRNA is selected from the group consisting of miR-19a, miR-29a, miR-29b, miR29c, miR-92a, and precursors or derivatives thereof. In certain embodiments, the other microRNA is miR-19a and/or miR-92a, or precursor(s) or derivative(s) thereof. In other embodiments, the other microRNA is miR-29a, miR-29b, and/or miR-29c, or precursor(s) or derivative(s) thereof.

In one embodiment, the invention is directed to the treatment and/or prevention of hepatic fibrosis associated with chronic Hepatitis B, Hepatitis C, non-alcoholic steatohepatitis (NASH), alcoholic liver disease, metabolic liver diseases (Wilson's disease, hemochromatosis), biliary obstruction (congenital or acquired) or liver diseases associated with fibrosis of unknown cause.

The miR-19b nucleic acid or analog described above is preferably employed for therapeutic uses in combination with a suitable pharmaceutical carrier. Such compositions comprise an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids some of which are described herein. In one embodiment, the pharmaceutical carrier may comprise a virus, a liposome, or a polymer.

The administration of a pharmaceutical composition comprising miR-19b or a precursor or analog thereof may be carried out by known methods, wherein a nucleic acid is introduced into a desired target cell in vitro or in vivo. In general, methods of administering nucleic acids are well known in the art. In particular, the routes of administration already in use for nucleic acid therapeutics, along with formulations in current use, provide preferred routes of administration and formulation for the administration of miR-19b compositions of the invention.

miR-19b compositions can be administered by a number of routes including, but not limited to: oral, intravenous, intraperitoneal, intramuscular, transdermal, subcutaneous, topical, sublingual, or rectal means. Nucleic acids can also be administered via liposomes. Such administration routes and appropriate formulations are generally known to those of skill in the art.

Administration of the formulations described herein may be accomplished by any acceptable method which allows the miR-19b or a precursor or analog thereof to reach its target. The particular mode selected will depend of course, upon factors such as the particular formulation, the severity of the state of the subject being treated, and the dosage required for therapeutic efficacy. As generally used herein, an "effective amount" of a nucleic acids is that amount which is able to treat one or more symptoms of fibrosis or related disease, reverse the progression of one or more symptoms of fibrosis or related disease, halt the progression of one or more symptoms of fibrosis or related disease, or prevent the occurrence of one or more symptoms of fibrosis or related disease in a subject to whom the formulation is administered, as compared to a matched subject not receiving the compound or therapeutic agent. The actual effective amounts of drug can vary according to the specific drug or combination thereof being utilized, its particular formulation, the mode of administration, and the age, weight, condition of the patient, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. The composition can be injected intradermally for treatment or prevention of cancer, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

Preferably, the agent and/or nucleic acid delivery system are provided in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

In one embodiment, formulations comprising the miR-19b or a precursor or analog thereof may be administered via recombinant adeno-associated virus (rAAV). Typical administration dosages may range from about $2.0 \times 10^{10}$ to $1.0 \times 10^{11}$ vector genomes/kg.

In a further embodiment a nucleic acid encoding a miR-19b molecule or an analog thereof can be on a vector. These vectors include a sequence encoding a mature microRNA and in vivo expression elements. In a preferred embodiment, these vectors include a sequence encoding a pre-miRNA and in vivo expression elements such that the pre-miRNA is expressed and processed in vivo into a mature miRNA. In another embodiment, these vectors include a sequence encoding the pri-miRNA gene and in vivo expression elements. In this embodiment, the primary transcript is first processed to produce the stem-loop precursor miRNA molecule. The stem-loop precursor is then processed to produce the mature microRNA.

Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have general utility for the high-efficiency transduction of nucleic acids in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Cliffton, N.J. (1991).

In one embodiment, the composition comprising the miR-19b or a precursor or analog thereof can be perfused directly through the targeted tissue, such as the liver. For example, the composition containing the miR-19b can be perfused directly through a body organ containing fibrotic tissue, without introducing the miR-19b into the body's general circulation, removing them from the organ with effluent blood and transporting the contaminated blood to an extracorporeal circuit where the blood is treated to remove the contamination, and returning the treated blood to the body. In some embodiments, such a process may help prevent undesirable levels of the miR-19b or a precursor or analog thereof from entering the body's general circulation while delivering effective doses to the fibrotic organ. Methods of perfusing active agents through a body organ, such as the liver, are described in greater detail in U.S. Pat. No. 5,069,662, the contents of which are incorporated by reference in their entirety.

The formulations may be delivered using a bioerodible implant by way of diffusion or by degradation of a polymeric matrix. In certain embodiments, the administration of the formulation may be designed so as to result in sequential exposures to the miRNA over a certain time period, for example, hours, days, weeks, months or years. This may be accomplished, for example, by repeated administrations of a formulation or by a sustained or controlled release delivery system in which the miRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other suitable delivery systems include, but are not limited to, time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the miRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the miRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an conically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the miRNA employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

Therapeutic compositions comprising one or more nucleic acids (e.g., miR-19b) or analogs thereof are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the patient. Administration can be accomplished via single or divided doses.

In vitro and in vivo models can be used to determine the effective doses of the nucleic acids as a potential fibrosis treatment as is known to the skilled artisan.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers.

Any of the foregoing methods for preparing and/or administering miR-19b can be similarly employed to prepare and/or administer other microRNAs, particularly other microRNAs intended for use in combination with miR-19b.

In a further aspect, the present invention is directed to the use of miR-19b as a biomarker for fibrosis, particularly liver fibrosis. The inventors have observed that fibrotic liver tissue shows low to no detectable miR-19b expression in comparison to normal healthy liver tissue. Accordingly, measurements of the level of miR-19b in a tissue biopsy (e.g., a liver biopsy) can be used as a biomarker/indicator for fibrosis (e.g., hepatic fibrosis). Moreover, because of an inverse relationship between tissue and circulatory miRNA levels, the presence of miR-19b or elevated levels of miR-19b in the blood (e.g., serum or plasma) serves as a biomarker/indicator for tissue fibrosis (e.g., hepatic fibrosis).

In certain embodiments of the invention, the diagnosis or prognosis may be achieved by measuring the amount of miR-19b that is present at increased levels in the blood (e.g., serum or plasma) of a subject suspected of suffering from fibrosis. In some cases, the level of the miR-19b marker will be compared to a control to determine whether the level is increased. The control may be an external control, such as a miRNA in a blood (e.g., serum or plasma) sample from a subject known to be free of fibrosis. The external control may be a sample from a normal (non-diseased) subject. In other circumstances, the external control may be a miRNA from a non-blood sample like a tissue biopsy or a known amount of a synthetic RNA. The external control may be a pooled, average, or individual sample; it may be the same or different miRNA as one being measured. An internal control is a marker from the same sample being tested, such as a miRNA control. See, e.g., US Publication No. US 2009/0075258.

The following Examples are provided for the purpose of illustrating embodiments of the invention and should not be construed as limiting the invention in any way.

EXAMPLES

Materials and Methods

Human Tissue Samples

Human fibrotic liver biopsy samples (n=21) were obtained from the Liver Biliary-Pancreatic Program Repository at Carolinas Medical Center (Charlotte, N.C.). Informed consent forms were signed by each patient from which samples were collected and approval from the Institutional Review Board was obtained. Normal controls (n=7) were obtained from the Liver Tissue Cell Distribution Center (LTCDS) specimen bank (Minneapolis, Minn.).

miRNA Isolation, Purification and Microarray

Total RNA was isolated from samples using Trizol Reagent (Invitrogen, Carlsbad, Calif.) per manufacturer's instructions. The integrity of the RNA was verified by an Agilent 2100 Bioanalyzer profile (Agilent Technologies Inc., Santa Clara, Calif.). The RNA was Poly (A) tailed and ligated to biotinylated signal molecules using the FlashTag™ Biotin RNA labeling Kit (Genisphere, LLC, Hatfield, Pa.). An Enzyme Linked Oligosorbent Assay (ELOSA) QC assay was performed to verify labeling prior to array hybridization. Hybridization, washing, staining and scanning was performed using Affymetrix GeneChip® system instruments (Affymetrix, Santa Clara, Calif.). Affymetrix GeneChip® Operating Software (GCOS) version 1.4 was used to analyze microarray image data and to compute intensity values. Affymetrix .CEL files containing raw, probe-level signal intensities were analyzed using Partek Genomics Suite (Partek, St. Louis, Mo.). Robust multichip averaging (RMA) was used for background correction, quantile normalization and probeset summarization with median polish. Statistical difference was calculated by two-way ANOVA analysis with false discovery rate (FDR). Partek miRNA workflow was used to access TargetScan target prediction database to perform miRNA-mRNA target integration.

Primary Hepatic Stellate Cell Isolation, Culture and Imaging

Male Sprague Dawley rats (>500 g) were purchased from Charles River Laboratories (Wilmington, Mass.) and housed in facilities approved by the National Institutes of Health. All surgical procedures were reviewed and approved by Carolinas Medical Center Institutional Animal Care and Use Committee. Primary rat HSCs were isolated by pronase/collagenase perfusion digestion followed by subsequent density gradient centrifugation as previously described. Cell purity and viability were confirmed by autofluorescence and trypan blue staining respectively. HSCs were maintained in Dulbecco's modified Eagle medium supplemented with 10% fetal bovine serum (FBS), 100 U/ml penicillin and 100 g/ml streptomycin. Culture medium was replaced every 48 hrs unless otherwise described and cells incubated at 37° C. with 5% $CO_2$. To document morphological changes and representative images were captured using an Olympus IX71 microscope (Olympus America Inc., Center Valley, Pa.).

Quantitative Real-Time Polymerase Chain Reaction and Immunoblotting

For miRNA analysis, first-strand complementary DNA synthesis was performed using TaqMan® MicroRNA Reverse Transcription Kit primed with miR-specific primer (Applied Biosystems, Foster City, Calif.). Real-time quantitative RT-PCR (qRT-PCR) was performed using the TaqMan® MicroRNA Assays (Applied Biosystems), following the manufacturer's recommendations, with an ABI Prism 7500 Sequence Detection System using TaqMan® Universal Master Mix (Applied Biosystems). Fold change values were calculated by comparative Ct analysis and normalized to 4.5S rRNA concentrations. For mRNA analysis, total RNA was isolated from primary HSCs and cDNAs were synthesized as previously described. mRNA expression was measured by the CFX96 Real-Time PCR Detection System using 50 ng cDNA, gene-specific oligonucleotide primers (Supplementary Table 1) and IQ SYBR Green Supermix (BIO RAD, Hercules, Calif.). The ddCt method was used to calculate mRNA expression levels as normalized β-actin. Proteins were isolated and subject to SDS-PAGE electrophoresis and transferred to nitrocellulose membranes as previously described. Bradford assays were used to measure protein concentration and Ponceau S staining verified equal protein loading. After blocking, membranes were incubated with primary antibodies (β-actin and TGFβRII, Santa Cruz Biotechnology, Inc, Santa Cruz, Calif.; MeCP2, Abeam, Cambridge, Mass.; Type I Collagen, Meridian Life Sciences, Saco, Me.) overnight at 4° C. followed by incubation with HRP-conjugated secondary antibodies. Chemiluminescence was used to visualize immunoreactivity as previously described.

Transient Transfection

HSCs (day 6) were subject to transfection with mature miR-19b and negative control probes using Lipofectamine 2000 (Invitrogen; Carlsbad, Calif.) according to manufacturer's instructions. Briefly, cells were plated at a density of $1-4\times10^5$ cells/ml in standard culture medium following isolation. Cells were washed 3× with Opti-MEM I Reduced Medium prior to addition of transfection complexes. Lipofectamine-mimic complexes were incubated for 20 minutes and added to hepatic stellate cells in Opti-MEM at final concentrations of 25, 50 and 75 nM. After 6 hrs, transfection medium was aspirated and replaced with standard culture medium supplemented with 5% FBS. Recombinant TGFβ (Sigma-Aldrich; St. Louis, Mo.) was added at a concentration of 5 ng/ml after the 6 hr period. Dual luciferase vector (pEZX-MT01) containing the full length 3'UTR of TGFβRII was purchased from GeneCopoeia, Inc (Rockville, Md.). Following standard restriction digestion confirmation of control and TGFβRII 3'UTR containing vectors, HSCs (LX-2 cells which were kindly provided by Dr. Scott Friedman) were co-transfected in 100 mm dishes with 4.8 µg of reporter plasmids and mature miR-19b or negative control (75 nM) using Lipofectamine 2000 as described above. 48 hrs post-transfection culture medium was aspirated, protein was harvested and luciferase activity was analyzed using GeneCopoeia Luc-Pair miR Luciferase Assay system. Firefly luciferase was normalized to Renilla luciferase activity and ratios normalized to total protein as determined by Bradford assay.

Immunocytochemistry, In Situ Hybridization and Immunohistochemistry

Prior to transfection culture-activated HSCs were seeded onto glass coverslips. Cells were transfected as described above and fixed with 4% paraformaldehyde and stained with anti αSMA antibody from Millipore (rabbit monoclonal). The slides were visualized using Carl Zeiss confocal microscope (LSM 710) with magnification 200×.

Liver tissues were obtained from rats following bile-duct ligation or sham procedures. Sections (6 µm) were cut from all paraffin embedded tissues (RNase free). In situ hybridization was performed using mercury LNA™ detection probes, 5'-DIG and 3'-DIG labeled miR-19b according to manufacturer's instructions (Exiqon, Woburn, Mass.).

Statistical Analysis

Data are presented as mean±SEM as determined from at least three independent experiments. Statistical analyses were performed using one way analysis of variance or student's t-test where appropriate, with p values<0.05 considered significant and denoted by *.

Results miRNA Profiling in Quiescent and Activated Hepatic Stellate Cells

A total of 55 significantly differentially expressed miRNAs were identified by array analyses of quiescent (freshly isolated) and activated (day 14 of culture) HSCs. Validation of previously described miRNA expression levels was obtained, with miRs 16, 29abc, 150 and 194 all significantly downregulated during HSC activation (FIG. 1A). These experiments also identified ~20 novel miRNAs not previously reported in published array data available at the time of manuscript preparation. Further analysis of differentially expressed miRNAs revealed that members of the miR-17-92 cluster (19a, 19b, 92a) were significantly downregulated in the profibrotic activated phenotype. miR17-92 is located within a polycistronic transcript on human chromosome 13 and interestingly is upregulated in several cancers and inflammatory disease states. Recently this cluster was shown to be a potent inhibitor of TGFβ signaling through multiple points of inhibition. Direct effects on TGFβRII and cascading inhibition on SMAD proteins were observed in neuroblastoma cells. In silico analyses (TargetScan and miRanda prediction databases) predicted putative seed match sites for miR-19b on the 3'UTR of TGFβRII. qRT-PCR confirmed array data, verifying a 24 fold decrease of this miR in activated compared to quiescent HSCs (FIG. 1B). The expression profile of miR-19b and predicted target mRNA TGFβRII were followed over 14 days in culture and a significantly clear inverse relationship was observed (FIG. 1C) with a dramatic decrease seen in expression of the miR from quiescence to day 3 and a significant upregulation of TGFβRII.

miR-19b Negatively Regulates Profibrotic TGFβ Signaling

To examine a possible role for miR-19b in HSC-mediated fibrogenesis a well established in vitro model of culture activation was used as previously described. Activated HSCs were transfected with synthetic miR-19b (19b) or a miRNA mimic negative control (SCR) and following 24 or 48 hrs of transfection RNA and protein were harvested. Preliminary studies validated that the SCR sequence did not significantly affect expression of TGFβRII or invariant control β-actin compared to mock transfection (Lipofectamine 2000 alone) and was therefore used as a control calibrator for all experiments. Additionally, effective transfection was verified by qRT-PCR and consistent concentration dependent increases were observed in miR-19b relative to 4.5S rRNA expression (FIG. 8). TGFβRII mRNA levels at both 24 and 48 hrs post-transfection were significantly decreased compared to control, with greatest reductions seen when transfected with 75 nM miR-19b (FIGS. 2A and 2B). Protein expression of the receptor was also significantly blunted by forced expression of miR-19b (FIG. 2C). Fibrotic TGFβ signaling propagates through the SMAD family of transcriptional activators, and like TGFβRII, SMAD2 and SMAD3 are also upregulated following fibrotic liver injury. While RSMAD2/3 3'UTRs do not harbor putative miR-19b binding sites as predicted by TargetScan and miRanda, mRNA expression of SMAD3 is significantly downregulated after 48 hrs of miR-19b transfection (FIG. 2D). miR-19b is also predicted to bind to the 3'UTR of Co-SMAD4, but no significant changes were observed in SMAD4 mRNA expression following transfections, pointing to the specificity of miR-19b to the receptor (FIG. 9). Computational prediction of miR-19b binding to the 3'UTR of TGFβRII was validated by luciferase reporter assay (FIG. 2E). Addition of miR-19b mimic induced a 50-60% reduction in luciferase activity compared to controls.

miR-19b Decreases Expression of TGFβ Target Genes

In the hepatic microenvironment, TGFβ is a potent profibrogenic mediator regulating cellular wound healing responses, predominantly synthesis and deposition of type I collagen, therefore effects of increasing miR-19b on downstream TGFβ signaling target procollagen mRNA and protein were measured. Forced expression of miR-19b dampens mRNA expression of both procollagen Col1α1 and Col1α2, with more significant effects observed on the transcription of Col1α2 (FIGS. 3A and 3B). Translation of the fibrillar collagen is also markedly decreased after miR-19b treatment as denoted by a 40% decrease in intracellular protein expression observed after 48 hrs (FIG. 3C), confirming the negative regulation of TGFβRII signaling by miR-19b as either procollagen 3'UTR lack predicted binding sites (TargetScan). Additionally, functional secretion of this protein is also disrupted by miR-19b as determined by immunoblot utilizing proteins concentrated from harvested culture medium (48 hrs) (FIG. 10).

miR-19b Inhibits TGFβ Paracrine Signals

While autocrine signaling by the activated HSC is the dominant force behind sustained collagen expression during hepatic fibrosis, paracrine signaling from damaged neighboring hepatocytes and activated immune cells also stimulate TGFβ signal transduction in the HSC. As such, recombinant TGFβ1 was added to activated HSCs transfected with miR-19b mimics and levels of procollagen mRNA were determined. Verification of collagen stimulation by addition of recombinant TGFβ1 protein was performed (~2.2-3 fold increase in collagen mRNA compared to control, data not shown). After 24 hrs Col1α2 mRNA expression is decreased even in the presence of exogenous TGFβ and both procollagens are significantly decreased after 48 hrs of treatment as compared to respective control (FIG. 4), indicating a powerful role for miR-19b in the inflammatory hepatic microenvironment.

Markers of HSC Activation are Suppressed by miR-19b

Following liver injury, both blood and tissue TGFβ levels are elevated stimulating the fibrotic response and establishment of the activated phenotype of the HSC with concomitant increases in cytoskeletal protein αSMA and morphological transition of the quiescent phenotype to a myofibroblast-like cell. Interestingly, forced expression of miR-19b blunted the activated HSC phenotype as denoted by shrunken cytoplasm, decreased polygonal shape and increased spindle shaped cellular protrusions (characteristic of the quiescent phenotype) (FIG. 5A). Morphological changes indicative of suppression of the activated phenotype correlated with levels of αSMA mRNA, which were significantly decreased after 48 hrs of transfection even in the presence of exogenous rhTGFβ (FIGS. 5B and 5C). Immunoctyochemical analysis of αSMA protein expression corroborated the visible reduction in activated phenotype as visualized by markedly reduced red fluorescence as well as by disorganization and disorientation of actin fibers (FIG. 5D). Further, miR-19b restored GFAP expression, a marker of quiescent HSCs (FIG. 5E).

Recent epigenetic profiling of the HSC transdifferentiation process highlighted a role for methyl CpG binding protein MeCP2, which was significantly upregulated upon culture-activation. Mechanistically, MeCP2 is reported to aid in the epigenetic reprogramming of the HSCs through recruitment of silencing complexes to the promoter region of PPARγ (known to maintain HSC quiescence). As MeCP2 is also subject to miR-based regulation and the 3'UTR of MeCP2 harbors a putative binding site for miR-19b in rat, mouse and human sequences as predicted by TargetScan, levels of this epigenetic factor were assessed. Levels of MeCP2 mRNA and protein were significantly reduced with increased expression of miR-19b (FIGS. 5F and 5G), highlighting a broad anti-fibrotic role for this particular miRNA.

miR-19b is Decreased Following Fibrotic Liver Injury In Vivo

Next, we assessed whether decreased miR-19b also occurs in vivo (in intact animals), in a rat model of hepatic fibrosis. Tissue sections from sham operated control and BDL rats were subjected to in situ hybridization and qRT-PCR experiments to assess expression of miR-19b. miR-19b was markedly decreased in fibrotic liver tissue compared to controls (FIGS. 6A and B). miR-19b specific staining (red fluorescence, FIG. 6A) in control tissue appears outside of the parenchymal cells and higher magnification inspection is indicative of perisinusoidal (HSC-specific location) expression. Supporting in situ hybridization data, low expression of miR-19b, comparable to that of activated HSCs, were observed in primary rat hepatocytes as compared to quiescent HSCs (FIG. 6C). To confirm initial observations of HSC specific expression, co-localization of miR-19b (red fluorescence) and GFAP (green fluorescence), a quiescent HSC specific marker, was performed. Merged images (FIG. 6D) obtained from single channel images showed high intensity yellow fluorescence in Sham tissue, indicating miR-19b expression in quiescent HSCs. As expected, decreased yellow fluorescence was observed in BDL tissue (FIG. 6D).

Human Hepatic Fibrosis is Associated with Decreased miR-19b

Total RNA was isolated from fibrotic (Metavir fibrosis score of 3 or 4 due to varying etiologies including PBC, HCC and HCV) and normal control liver tissues. qRT-PCR was used to determine relative expression levels of miR-19b and as observed in the rodent fibrotic injury models, levels of miR-19b are also significantly decreased by approximately 80% in human patients with fibrotic livers (FIG. 7A). miR-19b levels were also assessed in the sera of fibrotic patients. When directly compared to pair-matched tissue levels, a clear inverse relationship was observed (FIG. 7B).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating liver fibrosis in a mammal in need thereof comprising contacting hepatic stellate cells (HSCs) in the liver of the mammal with a therapeutically effective amount of a composition comprising microRNA-19b (miR-19b) or a precursor or derivative thereof, wherein said miR-19b, or precursor or derivative thereof, inhibits activation of the HSCs.

2. The method of claim 1, wherein miR-19b or the precursor thereof comprises the sequence: 5' UGUGCAAAUCCA-UGCAAAACUGA-3'(SEQ ID NO: 1).

3. The method of claim 1, wherein the composition comprises a DNA precursor that encodes miR-19b.

4. The method of claim 1, wherein the composition further comprises a microRNA selected from the group consisting of miR-19a, miR-29a, miR-29b, miR29c, miR-92a, and precursors or derivatives thereof.

5. The method of claim 1, wherein the composition inhibits expression of a gene and/or protein in the HSCs, wherein the gene and/or protein is selected from the group consisting of transforming growth factor beta (TGFβ) receptor II (TGF-βRII), RSMAD3, Collagen 1α1 (Col1α1), Collagen 1α2 (Col1α2), Type I Collagen, smooth muscle α-actin (αSMA), MeCP2, Furin, CTGF, THBS1 and KLF10.

6. The method of claim 5, wherein the gene and/or protein expression is inhibited by at least 10%, 15%, 20%, 25%, 30%, 35%, 40%, 45%, 50%, 55%, 60%, 65%, 70%, 75%, 80%, 85%, 90%, 95%, or more.

7. The method of claim 1, wherein the mammal is a human.

8. The method of claim 1, wherein the mammal suffers from at least one of chronic Hepatitis B, Hepatitis C, non-alcoholic steatophepatitis (NASH), alcoholic liver disease, a metabolic liver disease, Wilson's disease, hemochromatosis, or biliary obstruction.

9. A method for inhibiting activation of a hepatic stellate cell (HSC) comprising contacting a HSC with a composition comprising microRNA-19b (miR-19b) or a precursor or derivative thereof.

10. The method of claim 9, wherein miR-19b or the precursor thereof comprises the sequence: 5'-UGUGCAAAUC-CAUGCAAAACUGA-3'(SEQ ID NO: 1).

11. The method of claim 9, wherein the composition comprises a DNA precursor that encodes miR-19b.

12. The method of claim 9, wherein the composition further comprises a microRNA selected from the group consisting of miR-19a, miR-29a, miR-29b, miR29c, miR-92a, and precursors or derivatives thereof.

13. The method of claim 9, wherein the amount of miR-19b, or precursor or derivative thereof, in the composition is at least 25 nM, at least 50 nM, or at least 75 nM.

14. The method of claim 9, wherein the composition inhibits expression of at least one gene and/or protein in the HSC, wherein the gene and/or protein is selected from the group consisting of TGFβRII, RSMAD3, Collagen 1α1 (Col1α1), Collagen 1α2 (Col1α2), Type I Collagen, mooth muscle α-actin (αSMA), MeCP2, Furin, CTGF, THBS1 and KLF10.

15. The method of claim 14, wherein expression of the gene and/or protein is inhibited by at least 10%, 15%, 20%, 25%, 30%, 35%, 40%, 45%, 50%, 55%, 60%, 65%, 70%, 75%, 80%, 85%, 90%, 95%, or more.

16. A method for inhibiting expression of TGFβRII in a hepatic stellate cell (HSC) comprising contacting the HSC with a composition comprising miR-19b or a precursor or derivative thereof.

17. The method of claim 16, wherein miR-19b or the precursor thereof comprises the sequence: 5'-UGUGCAAAUC-CAUGCAAAACUGA-3'(SEQ ID NO: 1).

18. The method of claim 16, wherein the composition comprises a DNA precursor that encodes miR-19b.

19. The method of claim 16, wherein the amount of miR-19b, or precursor or derivative thereof, in the composition is at least 25 nM, at least 50 nM, or at least 75 nM.

20. A method for characterizing liver fibrosis in a patient comprising: measuring a level of miR-19b in a serum sample, and determining whether the level of miR-19b in the serum sample is decreased or elevated as compared to a control sample, thereby characterizing fibrosis in the patient.

21. The method of claim 20, wherein an elevated level of miR-19b in the serum sample as compared to the control sample indicates that the patient is suffering from hepatic fibrosis.

22. The method of claim 1, wherein the amount of miR-19b, or precursor or derivative thereof, in the composition is at least 25 nM, at least 50 nM, or at least 75 nM.

23. The method of claim 1, wherein the miR-19b, or precursor or derivative thereof, is delivered to the HSCs by a recombinant adeno-associated virus (rAAV).

24. The method of claim 1, wherein the miR-19b, or precursor or derivative thereof, is covalently linked to a carrier that improves cellular delivery.

25. The method of claim 1, wherein the composition is perfused directly through the liver.

* * * * *

UNITED STATES PATENT AND TRADEMARK OFFICE
CERTIFICATE OF CORRECTION

PATENT NO. : 8,759,313 B2
APPLICATION NO. : 13/566138
DATED : June 24, 2014
INVENTOR(S) : Schrum et al.

It is certified that error appears in the above-identified patent and that said Letters Patent is hereby corrected as shown below:

On the Title Page,
Item [73]: "The Charlotte-Mecklenburg Hospital Authority" should read --The Charlotte-Mecklenburg Hospital Authority d/b/a Carolinas HealthCare System--.

Signed and Sealed this
Twenty-eighth Day of October, 2014

Michelle K. Lee
*Deputy Director of the United States Patent and Trademark Office*